US00PP18567P3

(12) United States Plant Patent
Quemard

(10) Patent No.: US PP18,567 P3
(45) Date of Patent: Mar. 4, 2008

(54) ***SYMPHORICARPOS* PLANT NAMED 'BRAIN DE SOLEIL'**

(50) Latin Name: *Symphoricarpos×Chenaultii*
Varietal Denomination: Brain De Soleil

(75) Inventor: Pascal Quemard, Brain sur I' Authion (FR)

(73) Assignee: Selection New Plant Sarl, Le Luc (FR)

( * ) Notice: Subject to any disclaimer, the term of this patent is extended or adjusted under 35 U.S.C. 154(b) by 0 days.

(21) Appl. No.: 11/392,492

(22) Filed: Mar. 30, 2006

(65) Prior Publication Data

US 2006/0225170 P1 Oct. 5, 2006

(30) Foreign Application Priority Data

Mar. 31, 2005 (EM) ..... 2005/0625

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
*Assistant Examiner*—S. B. McCormick-Ewoldt
(74) *Attorney, Agent, or Firm*—Buchanan Ingersoll & Rooney PC

(57) ABSTRACT

A new and distinct variety of *Symphoricarpos×Chenaultii* plant, commonly known as Chenault Coralberry, is provided. The new variety originated as a naturally occurring mutation of the 'Hancock' variety (non-patented in the United States) at Maine et Loire, France. Unlike the parental variety, the new variety forms attractive yellow-orange foliage. The new variety is low-growing and displays a ground cover growth habit. The distinctive combination of characteristics renders the new variety to be well suited for growing as attractive ornamentation in the landscape.

1 Drawing Sheet

Figure 1:
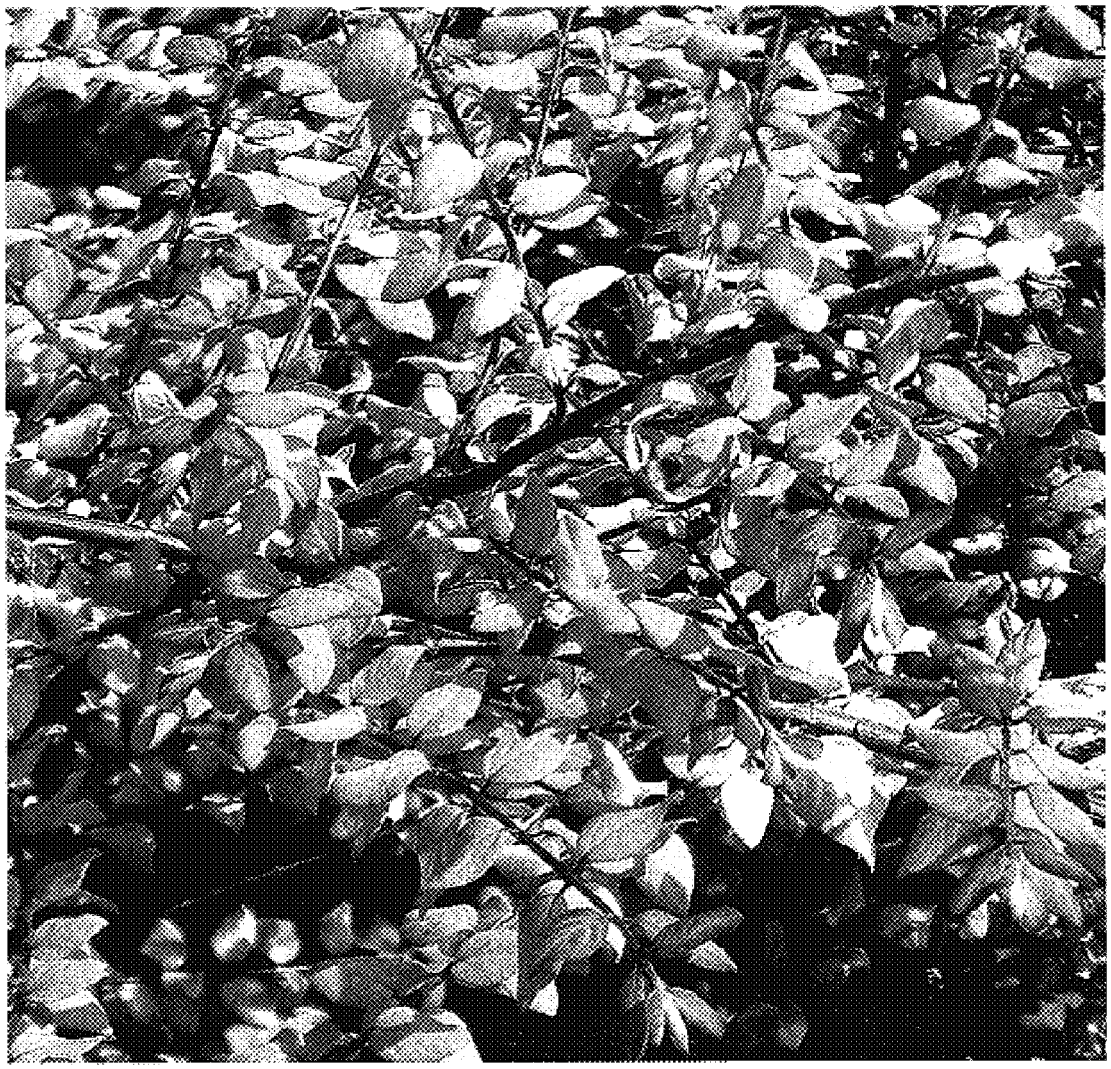

Botanical/commercial classification: *Symphoricarpos×Chenaultii*/Chenault Coralberry.
Varietal denomination: cv. Brain De Soleil.

SUMMARY OF THE INVENTION

A new variety of *Symphoricarpos* plant, botanically known as *Symphoricarpos×Chenaultii* is provided.

The new variety of the present invention was discovered during 2003 at Maine et Loire, France, while growing among plants of the 'Hancock' variety (non-patented in the United States). The new variety is a natural mutation of the 'Hancock' variety of unknown causation. I was primarily attracted to the plant of the new variety in view of it is distinctive foliage coloration. Had I not discovered and preserved the plant of the new variety it would have been lost to mankind.

I was found that the plant of the new variety exhibits the following combination of characteristics:

(a) displays attractive yellow-orange foliage unlike the green foliage of its parent 'Hancock' variety (non-patented in the United States), (b) displays a ground cover growth habit, and (c) is well suited for growing as attractive ornamentation in the landscape.

The new variety of the present invention readily can be distinguished from other *Symphoricarpos×Chenaultii* varieties, including its parent of the 'Hancock' variety in view of its distinctive foliage coloration.

The new variety well meets the needs of the horticultural industry and is particularly well suited for providing attractive ornamentation in the landscape.

The new variety of the present invention has been found at Maine et Loire, France, to undergo asexual propagation by the rooting of cuttings. A cutting has been found to initiate rooting in approximately one month. The distinctive combination of characteristics of the new variety is reliably transmitted to subsequent generations following such propagation. Accordingly, the new variety propagates in a true-to-type manner via asexual propagation.

The new variety has been named 'Brain De Soleil'.

BRIEF DESCRIPTION OF THE PHOTOGRAPH

The accompanying photograph of FIG. 1 depicts the attractive yellow-orange foliage and red-brown branches of a typical plant of the new variety. Such plant was approximately two years of age and was growing in the landscape during the summer at Maine et Loire, France.

DETAILED DESCRIPTION

The following description is based on the observation of a two-year-old specimen of the new variety growing outdoors at Maine et Loire, France. Color designations are with reference to the R.H.S. Colour Chart of the Royal Horticultural Society, London, England. When employed, common color terms are to be accorded their customary dictionary significance.

Origin: A natural mutation of the 'Hancock' variety (non-patented in the United States) of unknown causation.

Plant:

*Habit.*—Spreading as a ground cover.

*Height.*—Commonly approximately 50 to 60 cm on average.

*Width.*—Commonly approximately 100 to 150 cm on average.

Branches:

*Length.*—Typically approximately 30 cm on average.

*Diameter.*—Typically approximately 3 mm on average.

*Internode length.*—Typically approximately 15 to 25 mm on average.

*Quantity.*—Numerous and very dense.

*Texture.*—Smooth.

*Color.*—Red-brown, mature branches commonly are near Greyed-Orange Group 174B, and young branches commonly are near Greyed-Purple Group 186A.

Foliage:

*General appearance.*—The foliage is deciduous, shoots change from yellow to orange in coloration at full maturity, and the brightness varies somewhat with the season.

*Leaf size.*—Length: commonly approximately 1 to 1.5 cm on average. Width: commonly approximately 0.8 to 1 cm on average.

*Arrangement.*—Distichous.

*Leaf shape.*—Ovate.

*Leaf apex.*—Acuminate.

*Leaf base.*—Rounded.

*Leaf margin.*—Fine, simple, and regular serration.

*Venation.*—Typical of species.

*Petiole.*—Commonly approximately 2 mm in length on average and approximately 0.3 mm in diameter on average.

*Leaf color.*—Springtime: primarily near Orange-Red Group 31A and 31B and Red Group 37A and 37B on the upper surface and tends to be more uniform on the under surface. Summer: primarily near Yellow Group 10B and 10C on the upper surface and the under surface. December: primarily near Yellow-Orange Group 15B and Yellow-Orange Group 16A.

Inflorescence:

*Time of blooming.*—May.

*Duration of blooming.*—Approximately one month depending upon environmental conditions.

*Size.*—Very small, approximately 2 mm in diameter, and inconspicuous.

*Quantity.*—Sparse.

*Hip size.*—Commonly 0.5 to 0.8 cm on average.

*Hip color.*—Near Red-Purple Group 61B and 61C.

*Shape.*—Tubular with four or five lobes.

*Petal number.*—Five.

*Petal color.*—Near White Group 155D and sometimes very lightly suffused with Red-Purple Group 64D.

*Sepals.*—Typical of the species.

*Peduncle.*—Commonly approximately 1 mm in length on average, approximately 0.2 mm in diameter on average, and near Greyed-Purple Group 184A in coloration.

The winter hardiness is good with plants having well withstood winter temperatures of −25° C. The response to heat and drought is somewhat weak during observations to date.

During observations to date the resistance to disease has been excellent under the growing conditions of Maine et Loire, France.

Plants of new 'Brain De Soleil' variety have not been observed under all possible environmental conditions to date. Accordingly, it is possible that the phenotypic expression may vary somewhat with changes in light intensity and duration, cultural practices, and other environmental conditions.

What is claimed is:

1. A new and distinct *Symphoricarpos*×*Chenaultii* plant that exhibits the following combination of characteristics:

(a) displays attractive yellow-orange foliage unlike the green foliage of its parent 'Hancock' variety (non-patented in the United States), (b) displays a ground cover growth habit, and (c) is well suited for growing as attractive ornamentation in the landscape;

substantially as illustrated and described.

* * * * *